US006764855B2

(12) United States Patent
Roman et al.

(10) Patent No.: US 6,764,855 B2
(45) Date of Patent: Jul. 20, 2004

(54) FLUORESCENT HPLC ASSAY FOR 20-HETE AND OTHER P-450 METABOLITES OF ARACHIDONIC ACID

(75) Inventors: Richard J. Roman, Brookfield, WI (US); Kristopher G. Maier, Milwaukee, WI (US)

(73) Assignee: MCW Research Foundation, Milwauke, WI (US)

(*) Notice: Subject to any disclaimer, the term of this patent is extended or adjusted under 35 U.S.C. 154(b) by 14 days.

(21) Appl. No.: 10/257,014

(22) PCT Filed: Apr. 6, 2001

(86) PCT No.: PCT/US01/11321
§ 371 (c)(1),
(2), (4) Date: Feb. 14, 2003

(87) PCT Pub. No.: WO01/77674
PCT Pub. Date: Oct. 18, 2001

(65) Prior Publication Data
US 2003/0211623 A1 Nov. 13, 2003

Related U.S. Application Data
(60) Provisional application No. 60/196,076, filed on Apr. 10, 2000.

(51) Int. Cl.$^7$ ................................................ G01N 21/64
(52) U.S. Cl. ........................... 436/71; 436/86; 436/161; 436/172
(58) Field of Search ........................... 436/71, 86, 161, 436/172; 210/662

(56) References Cited

U.S. PATENT DOCUMENTS

| | | | | |
|---|---|---|---|---|
| 5,773,300 A | * | 6/1998 | Federighi et al. | 436/64 |
| 5,780,237 A | * | 7/1998 | Bursten et al. | 435/7.1 |
| 5,989,844 A | | 11/1999 | Shimada et al. | |
| 6,420,131 B1 | * | 7/2002 | Miller et al. | 435/25 |
| 6,534,282 B2 | * | 3/2003 | Kim et al. | 435/7.92 |

OTHER PUBLICATIONS

Reynaud, D et al. "Improved high–performance liquid chromatographic method for the combined analysis of phospholipase, lipoxygenase and cyclooxygenase activities" J. Chrom. vol. 762, Iss. 2 (Oct. 25, 2001), pp. 175–180.*
Alonso–Galicia M et al., "20–HETE agonists and atagonists in the renal circulation." Physiol Renal *Physiol 277*: F790–F796 (1999).
Amet Y et al., "Simultaneous radiometric and fluorimetric detection of lauric acid metabolites *using high–performance liquid chromatography following esterification with* 4–bromomethyl–6,7–dimethoxycoumarin . . . " J Chromatog B Biomed Appl 68: 233–239 (1996).
Balestrieri C et al., "Measurement of Platelet–Activating Factor Acetyhydrolase Activity by *Quantitative High–Performance Liquid Chromatography Determination of Coumarin–Derivatized* 1–0–Alkyl–2–sn–lysoglyceryl–3–phosphorylcholine." Anal Biochem. 233: 145–150 (1996).

Brekke OL et al., "Tumor necrosis factor–induced release of endogenous fatty acids analyzed by a *highly sensitive high–performance liquid chromatography method*." J Lipid Res 38: 1913–1922 (1997).

Demin, P., et al., "Extractive Derivatization of the 12–Lipoxygenase Products, Hepoxilins, and *Related Compounds into Fluorescent Anthryl Esters for Their Complete High–Performance Liquid* Chromatography Profiling in Biological Systems." Analytical Biochemistry. 226, 252–255, 1995.

Kiss, L. et al., "Simultaneous Analysis of 4– and 5–Series Lipoxygenase and Cytochrome P450 *Products from Different Biological Sources by Reversed–Phase High–Performance Liquid* Chromatographic Technique." Analytical Biochemistry 261: 16–28, 1998.

Maier, KG et al., "Fluorescent HPLC assay for 20–HETE and other P–450 metabolites of *arachidonic acid.*" *Am. J. Physiol. Heart Cir. Physiol. 279*: H863–H871, 2000.

Maier, KG, et al., "A rapid, sensitive fluorescent HPLC assay for HETEs and EETs." Abstract for *Annual meeting of professional research scientists: experimental biology 2000*; San Diego, CA. FASEB Journal vol. 14, No. 4 p. A140.

Metori, A., et al., "Quantitation of Monohydroxy Fatty Acids by High–Performance Liquid Chromatography with Fluorescence Detection." J Chromatography, 622, 147–151, 1993.

Mingrone, G., et al., "Reversed–Phase High–Performance Liquid Chromatographic Separation and Quantification of Individual Human Bile Acids." J Chromatography. 183, 277–286, 1980.

Niumra, N., et al., "Fluorescent Labeling of Fatty Acids with 9–Anthryldiazomethane (ADAM) for High Performance Liquid Chromatography." Analytical Letters, 13(A3), 191–202, 1980.

(List continued on next page.)

Primary Examiner—Jeffrey R. Snay
(74) Attorney, Agent, or Firm—Quarles & Brady LLP

(57) ABSTRACT

The present invention provides a fluorescent HPLC assay for detecting the presence and/or measuring the level of 20-hydroxyeicosatetraenoic acid (20-HETE) and other P-450 metabolites of arachidonic acid in a sample. P-450 metabolites of arachidonic acid are first extracted from the sample and then labeled with 2-(2,3-naphthalimino)ethyl trifluoromethanesulfonate. The labeling reaction is catalyzed by N,N-diisopropylethylamine. Next, the labeled P-450 metabolites are separated on a 4.5×250-mm, 5 µM particle size C18 reverse-phase HPLC column using a mobile phase of methanol:water:acetic acid (82:18:0.1, v/v/v) and an isocratic elution at a rate of about 1.3 ml per minute. Fluorescence intensities of the column eluent are monitored by a fluorescence detector. Quantitation of P-450 metabolites in a sample can be made by using an internal standard.

25 Claims, 6 Drawing Sheets

OTHER PUBLICATIONS

Pratt, P.F., Jr., "Characterization of Epoxyeicosatrienoic Acids As Endothelium–Derived Hyperpolarizing Factors." Dissertation, Medical College of Wisconsin, 81–82, 150–155, & 168, 1997.

Voelter, W., et al., "Fluorescence Labeling in Trace Analysis of Biological Samples. Simultaneous Determination of Free Fatty Acids and Related Carboxylic Compounds." J Chromatography, 217, 491–507, 1981.

Yasaka, Y., et al., "2–(2,3–Naphthalimino)Ethyl Trifluoromethanesulphonate As a Higly Reactive Ultraviolet and Fluorescent Labelling Agent for the Liquid Chromatographic Determination of Carboxylic Acids." Elsevier Science Publishers B.V., 133–140, 1990.

Yakasaka, Y., et al., "Labeling of Free Carboxyl Groups." J Chromatography B, 139–155, 1994.

* cited by examiner

FLUORESCENT HPLC ASSAY FOR 20-HETE AND OTHER P-450 METABOLITES OF ARACHIDONIC ACID

CROSS-REFERENCE TO RELATED APPLICATIONS

This application claims the benefit of U.S. provisional application, Serial Number 60/196,076, filed on Apr. 10, 2000, which is incorporated herein by reference.

STATEMENT REGARDING FEDERALLY SPONSORED RESEARCH OR DEVELOPMENT

This invention was made with United States government support awarded by the following agency: NIH Grant No: HL 29587, HL-36279, GM-31278, and HL-59996. The United States has certain rights in this invention.

CROSS-REFERENCE TO RELATED APPLICATIONS

Not applicable.

BACKGROUND OF THE INVENTION

A variety of diseases such as salt sensitive hypertension, toxemia of pregnancy, asthma, hepatorenal syndrome, diabetes and subarachnoid hemorrhage are associated with abnormalities in arachidonic acid ("AA") metabolism. Recent studies have indicated that AA is primarily metabolized in the brain, kidney, lung, and vasculature by cytochrome P-450 enzymes to epoxyeicosatrienoic acids (EETs), dihydroxyeicosatrienoic acids (diHETEs), and 19- and 20-hydroxyeicosatetraenoic acids (19- and 20-HETE). McGiff J C and Quilley J, *Am J Physiol Regulatory Integrative Comp Physiol* 277: R607–R623 (1999); Roman R J and Alonso-Galicia M, *News Physiol Sci* 14: 238–242 (1999). 20-HETE and EETs are biologically active and have been implicated as paracrine factors and/or second messengers in the regulation of vascular tone, sodium and water excretion in the kidney, and airway resistance. McGiff J C and Quilley J, *Am J Physiol Regulatory Integrative Comp Physiol* 277: R607–R623 (1999); Roman R J and Alonso-Galicia M, *News Physiol Sci* 14: 238–242 (1999). Despite the importance of P-450 metabolites of AA, very little is known about the regulation of the concentrations of these mediators in tissue and biological fluids. Part of the problem has been the lack of a sensitive, inexpensive, and high-throughput assay to measure the endogenous concentration of these compounds. To date, gas chromatography-mass spectroscopy (GC-MS) with selective ion monitoring and one report of a fluorescent enzyme based immunoassay ("EIA") for EETs have been the only methods available to measure the concentration of P-450 metabolites of AA in biological samples. Capdevila J H et al. *J Biol Chem* 267: 21720–21726(1992); Catella F et al., *Proc Natl Acad Sci USA* 87: 5893–5897 (1990); Prakash C et al., *Biochem Biophys Res Commun* 185: 728–733 (1992); Schwartzman M L et al., *Biochem Biophys Res Commun* 180: 445–449 (1991); Toto R et al., *Biochem Biophys Acta* 191: 132–134 (1987). The EIA requires a specific antibody that is no longer generally available and, therefore, the assay cannot be reproduced in other labs. GC-MS has been successfully used to measure 20-HETE and EETs in the urine of humans and rats, and the reported concentration of these mediators is in the range of 0.5–5 ng/ml. The urinary excretion of EETs has been reported to increase in rats fed a high-salt diet and in patients with toxemia of pregnancy. Capdevila J H et al., *J Biol Chem* 267: 21720–21726 (1992); Oyekan A O et al., *J Clin Invest* 104:1131–1137(1999); Catella F et al., *Proc Natl Acad Sci USA* 87: 5893–5897 (1990). Moreover, the urinary excretion of 20-HETE is elevated in patients with hepatorenal syndrome and in DOCA-salt hypertensive rats. Sacerdoti D et al., *J Clin Invest* 100: 1264–1270 (1997); Oyekan A O et al., *Am J Physiol Regulatory Integrative Comp Physiol* 176: R766–R775 (1999).

Although GC-MS is a reliable method for the measurement of P-450 metabolites of AA, the high cost for the purchase and maintenance of the instrumentation and difficulties in preparing the samples for analysis have limited the use of this technique. Indeed, the preparation of urine samples for GC-MS involves an organic extraction of the lipid fraction, separation of the EETs or HETEs fractions by thin-layer chromatography and reverse-phase HPLC, derivatization of the samples to the methyl or pentabenzylfluoro esters, and conversion of these esters to trimethylsilyl derivatives. Toto R et al., *Biochem Biophys Acta* 191: 132–134 (1987). It also requires the synthesis and addition of a deuterated internal standard to the samples to correct for variable extraction and derivatization efficiencies. The extensive sample preparation reduces sample recoveries and the detection limits of this technique to the nanogram range. Oyekan A O et al., *J Clin Invest* 104: 1131–1137 (1999); Schwartzman M L et al., *Biochem Biophys Res Commun* 180: 445–449 (1991); Toto R et al. *Biochem Biophys Acta* 191: 132–134 (1987). GC-MS is also limited to the measurement of a single compound at a time.

In the last few years, many fluorescent HPLC-based methods have been described for the analysis of fatty acids following derivatization of the carboxyl or hydroxyl groups with agents such as anthryldiazomethane (ADAM), pyrenyldiazomethane (PDAM), bromomethyl- and diethylaminocoumarin, 2-(2,3-naphthalimino)ethyl trifluoromethanesulfonate and other dyes. Brekke O L et al., *J Lipid Res* 38: 1913–1922 (1997); Amet Y et al.,*J Chromatog B Biomed Appl* 68: 233–239 (1996); Minkler P E et al., *Anal Biochem* 231: 315–322 (1995); Yasaka Y and Tanaka M, *J Chromatog B Biomed Appl* 659:139–155 (1994); Yasaka Y et al., *J Chromatog* 508:133 (1990). Some of these studies have reported detection limits <10 pg for prostaglandins and fatty acids. The main problems associated with these methods have been difficulties in obtaining consistent derivatization for lack of good catalysts, the inability to clearly resolve all of the P450 metabolites of AA found in biologic samples by HPLC after these compounds have been reacted with a fluorescent compound, and the lack of an internal standard with an extraction and labeling efficiency identical to the compounds of interest.

BRIEF SUMMARY OF THE INVENTION

The present invention provides a fluorescent HPLC assay for simultaneously detecting the presence and/or measuring the level of 20-hydroxyeicosatetraenoic acid (20-HETE) and other P-450 metabolites of AA in a sample. P-450 metabolites of AA are first extracted from the sample and then labeled with 2-(2,3-naphthalimino)ethyl trifluoromethanesulfonate, a fluorescent material. The labeling reaction is catalyzed by N,N-diisopropylethylamine. Next, the labeled P-450 metabolites are separated on a 4.5×250-mm, 5 $\mu$M particle size C18 reverse-phase HPLC column using a mobile phase of methanol:water:acetic acid (82:18:0.1, v/v/v) and an isocratic elution at a rate of about 1.3 ml per minute. Fluorescence intensities of the column eluent are monitored by a fluorescence detector.

When quantitation of P-450 metabolites in a sample is desired, a known amount of an internal standard is added to the sample before the extraction of P-450 metabolites from the sample. The amount of a P-450 metabolite in the sample can be calculated from the ratio of the P-450 metabolite peak to the internal standard peak. When the HPLC assay of the present invention is used for detecting the presence of a P-450 metabolite in a sample, the use of an internal standard is optional.

The HPLC assay of the present invention can be used for clinical tests of urine, blood, plasma, cerebrospinal fluid, bronchiolar lavage fluid and tissues for the diagnosis of diseases associated with abnormalities in the formation and/or levels of P450 metabolites of AA such as salt sensitive hypertension, toxemia of pregnancy, asthma, hepatorenal syndrome, diabetes and subarachnoid hemorrhage.

It is an object of the present invention to provide a method to simultaneously analyze more P-450 metabolites of AA in a sample than prior art methods.

It is a feature of the present invention that the catalyst for the labeling reaction allows the labeling of P-450 metabolites with a high degree of consistency.

It is an advantage of the present invention that the method has a high degree of intra-assay reproducibility.

It is another advantage of the present invention that the method has a high degree of quantitation sensitivity.

It is yet another advantage of the present invention that the method is relatively simple and inexpensive to perform.

Further objects, features and advantages of the invention will be apparent from the following detailed description when taken in conjunction with the accompanying claims and drawings.

DETAILED DESCRIPTION OF THE INVENTION

Figure 1:
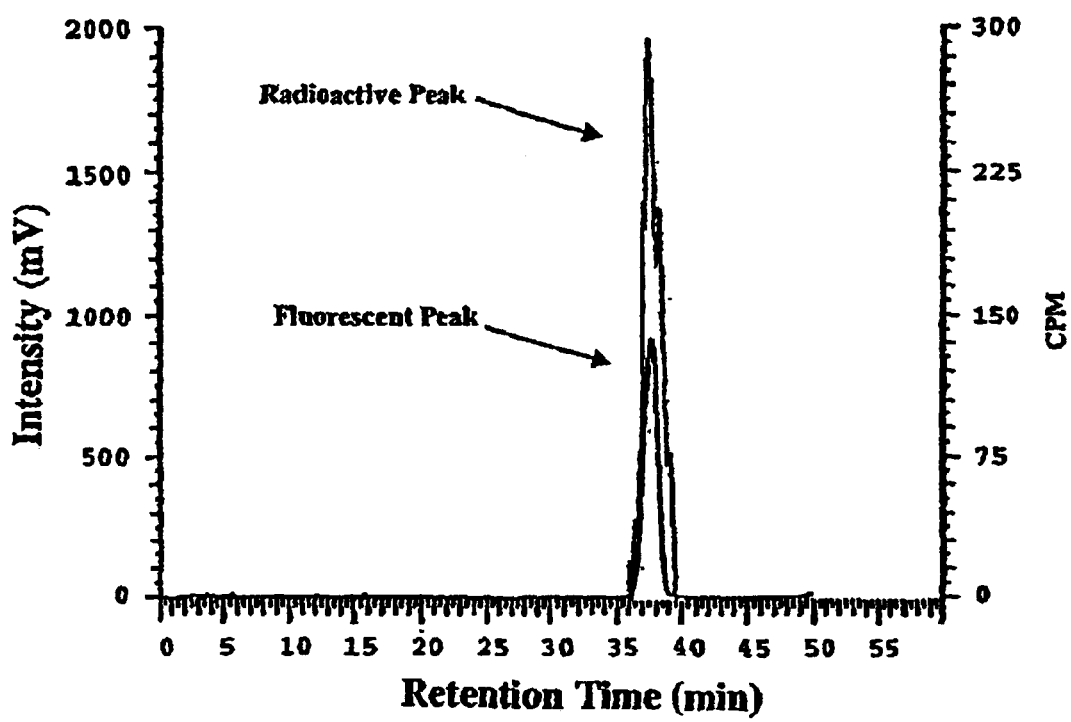
FIG. 1 shows a reverse-phase HPLC chromatogram demonstrating coelution of fluorescent and radioactive peaks following derivatization of $^{14}$C-labeled 20-hydroxyeicosatetraenoic acid [20-HETE; 10,000 counts/min (cpm)] with 2-(2,3-naphthalimino)ethyl trifluoromethanesulfonate.

The present invention provides a method for simultaneously analyzing 20-HETE and other P-450 metabolites of AA using HPLC. By "analyzing," we mean either detecting the presence and/or measuring the level of P-450 metabolites of AA. As shown in the examples below, the HPLC assay resolved not only 20-HETE from all other known P-450 metabolites of AA, including 19-, 18-, 16-, 15-, 12-, and 5-HETE, 5,6-diHETE and EETs, but also these other known P-450 metabolites of AA from each other with the exceptions of 17- and 16-HETE.

In one embodiment of the present invention, P-450 metabolites of AA from a biological sample are analyzed. By "biological sample," we mean a fluid or tissue from an animal or a human being, cultured cells or microorganisms, and medium or substrate used to culture the cells or microorganisms. Examples of a fluid from an animal or human being include but are not limited to urine, blood, plasma, cerebrospinal fluid and bronchiolar lavage fluid. Examples of a tissue from an animal or human being include but are not limited to renal tissue, brain tissue, lung tissue, liver tissue, breast tissue and biopsies from suspected cancerous tumors. In analyzing a biological sample, the sample is first extracted for lipids and the lipids are then labeled with a fluorescent material. Next the labeled lipid extract is loaded onto a HPLC column for separation of labeled P-450 metabolites of AA, which is followed by detection of labeled P-450 metabolites of AA.

Methods of extracting lipids from a biological sample are known in the art. One method that can be used is described in detail below. It is appreciated that other lipid extraction methods can also be used. Preferably, as described below, the lipid extract is further purified before fluorescence labeling.

To fluorescently label the lipids, a fluorescent material and the lipids are reacted with each other under the help of a catalyst. Many prior art fluorescent materials can label the lipids. For example, 9-ADAM, 1-ADAM, PDAM, 7-diethylaminocoumarin, and 4-bromomethyl-6,7-dimethoxycoumarin can be used to derivatize the samples using previously published techniques. Nimura N and Kinoshita T, *Anal Lett* 13: 191–202 (1980); Metori A et al, *J Chromatog* 622: 147–151 (1993); Brekke O L et al., *J Lipid Res* 38: 1913–1922 (1997); Balestrieri C et al., *Anal Biochem.* 233: 145–150 (1996); Amet Y et al. *J Chromatog B Biomed Appl* 68: 233–239(1996). However, when labeled with these materials, 20-HETE cannot be resolved from other HETEs (15-, 12-, 5-) and 5,6-diHETEs using normal phase, C18, or C8 reverse-phase HPLC. When resolving 20-HETE from other HETEs (15-, 12-, 5-) and 5,6-diHETEs is not critical for a particular assay, the above labeling material can be used.

As described below, a fluorescence label material that allows the resolution of the above closely related HETE structures is 2-(2,3-naphthalimino)ethyl trifluoromethanesulfonate. Any method that can label a lipid sample with 2-(2,3-naphthalimino)ethyl trifluoromethanesulfonate may be used in the present invention. For example, 20-HETE and other P-450 metabolites may be labeled with 2-(2,3-naphthalimino)ethyl trifluoromethanesulfonate according to the method of Yasaka et al. using potassium fluoride and 18-crown-6 or tetraethylammonium carbonate as a catalyst. Yasaka Y et al., *J Chromatog* 508: 133 (1990). This technique works well with standards dissolved in organic solvents. However, the labeling of biological samples is very inconsistent because the reaction is inhibited by moisture. Thus, it is preferable to use a catalyst that efficiently labels fatty acids even in the presence of moisture. The present invention provides that N,N-diisopropylethylamine is such a catalyst, which allows consistent labeling of fatty acids by 2-(2,3-naphthalimino)ethyl trifluoromethanesulfonate.

After fluorescence labeling reaction is completed, it is preferable to purify the labeled lipids, e.g., to remove the non-reacted dyes, before loading the lipids onto a HPLC column.

The HPLC column used in the present invention is a 4.5×250-mm, 5 μM particle size C18 reverse-phase HPLC column. The mobile phase used to elute the P-450 metabolites of AA from the column is methanol:water:acetic acid with a volume ratio of about 82:18:0.1. The mobile phase passes through the column isocratically at a rate of about 1.3 ml per minute.

The fluorescence intensity of 20-HETE and other P-450 metabolites of AA eluted from the column is detected by a fluorescence detector.

When the HPLC method of the present invention is used to quantitate the amount of 20-HETE and other P-450 metabolites of AA, a known amount of an internal standard is added to the sample being analyzed. If the sample is a biological sample, an internal standard is added to the sample before the sample is extracted for lipids. Preferably, the internal standard used has a similar extraction and labeling efficiency as 20-HETE so that the amount of 20-BETE loaded on the column can be determined directly by comparing the ratio of the 20-BETE peak and the internal standard peak. As described below, WIT-002 and 19-hydroxynonadeca-5(Z),8(Z),11(Z),14(Z)-tetraenoic acid are suitable internal standards that have similar extraction and labeling efficiencies. However, a compound that is otherwise suitable as an internal standard such as 10-hydroxyhexadecanoic acid tridecanoic acid, 16-hydroxyhexadecanoic acid tridecanoic acid, 15-hydroxypentadecanoic acid and tridecanoic acid may also be used in the present invention even if they have different extraction and labeling efficiencies from 20-HETE. One of ordinary skill in the art knows however to correct for such differences. The calculation of the peak ratios and the amount of different P-450 metabolites of AA can be done manually or, preferably, aided by a computer.

The examples below show that 20-HETE quantitation sensitivity of the HPLC system of the present invention can reach as low as 1 to 10 ng when the fluorescence detector is set at a medium sensitivity (10×). This degree of sensitivity is more than enough for routine measurements of 20-HETE and other P-450 metabolites of AA in urine and renal tissue because the basal levels are about 10–100 ng/ml. However, when higher quantitation sensitivity is required, the fluorescence detector can be set at the high gain setting (100×) so that the sensitivity can reach 1–100 pg.

The method for simultaneously analyzing 20-HETE and other P-450 metabolites of AA provided by the present invention can be used for clinically diagnosing of a disease associated with abnormalities in the formation and/or levels of P450 metabolites of AA such as salt sensitive hypertension, toxemia of pregnancy, asthma, hepatorenal syndrome, diabetes and subarachnoid hemorrhage.

EXAMPLES

Methods

1. Reagents.

All chemicals used were of analytic or IPLC grade. The fluorescent probes, 2-(2,3-naphthalimino)ethyl trifluoromethanesulfonate, 9-ADAM, 7-diethylaminocoumarin, 1-ADAM, 4-bromomethyl-6,7-dimethoxycoumarin, and 3-PDAM were all purchased from Molecular Probes (Eugene, Oreg.). The catalyst N,N-diisopropylethylamine and 1-aminobenzotriazole (ABT) were purchased from Sigma Chemical (St. Louis, Mo.). 5,6-diHETE, 5,6-EET, and the 15-, 12-, and 5-HETE standards were from Biomol (Plymouth Meeting, Pa.). An internal standard, 19-hydroxynonadeca-5(Z),8(Z),11(Z),14 (Z)-tetraenoic acid, and 8,9-, 11,12-, and 14,15-diHETE, 16-, 18-, 19-, and 20-HETE, and 8,9-, 11,12- and 14,15-EET were synthesized by J. R. Falck (Univ. of Texas Southwestern Medical Center, Dallas, Tex.). Another internal standard, 20-5(Z),14(Z)-hydroxyeicosadienoic acid (WIT-002) was synthesized and kindly provided by Taisho Pharmaceutical (Saitama, Japan). HPLC-grade methanol was purchased from VWR (South Plainfield, N.J.), and acetic acid was purchased from Fisher Scientific (Pittsburgh, Pa.).

2. Lipid Extraction.

An internal standard (100 ng/ml) of a nonbiologically relevant hydroxy fatty acid such as WIT-002, 19-hydroxynonadeca-5(Z),8(Z),11(Z),14(Z)-tetraenoic acid, 10-hydroxyhexadecanoic acid, 16-hydroxyhexadecanoic acid, or 15-hydroxypentadecanoic acid was added to the samples. Alonso-Galicia M et al., *Physiol Renal Physiol* 277: F790–F796 (1999). The acidic lipids were extracted with 3 vols of ethyl acetate after 0.25 ml of urine, 100 μg of renal tissue homogenate, or 100 μl of buffer collected from a microdialysis probe was acidified to pH 3.0 with formic acid. The samples were dried down under argon, reconstituted in 0.5 ml of 20% acetonitrile:water (pH 3.0), and applied to a Sep-Pak Vac 1 cc (catalog no. WAT054955; Waters, Milford, Mass.) that was prewashed with 1 ml of water followed by 1 ml of acetonitrile and 1 ml of water. The column was washed twice with 1 ml of 30% acetonitrile::water to remove polar lipids and then eluted with 400 μl of 90% acetonitrile:water. The eluent was diluted with 900 μl of water and applied to a prewashed Sep-Pak Vac column and then eluted with 500 μl of ethyl acetate to capture the free fatty acids. The sample was taken to dryness under argon.

3. Fluorescent Labeling and HPLC Analysis of Lipids.

In preliminary experiments, standards and samples were derivatized with 9-ADAM, 1-ADAM, PDAM, 7-diethylaminocoumarin, and 4-bromomethyl-6,7-dimethoxycoumarin using previously published techniques. Nimura N and Kinoshita T, *Anal Lett* 13: 191–202 (1980); Metori A et al., *J Chromatog* 622: 147–151 (1993); Brekke O L et al., *J Lipid Res* 38: 1913–1922 (1997); Balestrieri C et al., *Anal Biochem.* 233: 145–150 (1996); Amet Y et al., *J Chromatog B Biomed Appl* 68: 233–239(1996). Although we were able to completely derivatize the samples, we could not find a solvent system that would resolve labeled 20-HETE from other HETEs (15-, 12-, 5-) and 5,6-diHETEs using normal phase, C18, or C8 reverse-phase HPLC. The only label that we found that was capable of resolving these closely related structures was 2-(2,3-naphthalimino)ethyl trifluoromethanesulfonate. We initially attempted to label 20-HETE and other P-450 metabolites according to the method of Yasaka et al. with 2-(2,3-naphthalimino)ethyl trifluoromethanesulfonate using potassium fluoride and 18-crown-6 or tetraethylanunonium carbonate as a catalyst. Yasaka Y et al., *J Chromatog* 508: 133 (1990). Although this technique works well with standards dissolved in organic solvents, the labeling of biologic samples is very inconsistent because the reaction is inhibited by moisture. We searched for another catalyst and found that N,N-diisopropylethylamine catalyzes this reaction much more consistently.

To label the fatty acids, we resuspended samples, which were extracted and dried under argon, in 20 μl of acetonitrile containing 36.4 mM 2-(2,3-naphthalimino)ethyl trifluoromethanesulfonate. N,N-diisopropylethylamine (10 μl) was added to catalyze the reaction. The sample was reacted for 30 min at room temperature. The reactions were dried down under argon, resuspended in 1 ml of 20% acetonitrile:water, and applied to a Sep-Pak Vac column. The column was washed with 6 ml of 50% acetonitrile:water solution to remove unreacted dye and eluted with 500 µl of ethyl acetate. The eluent was dried under argon, and the samples were resuspended in 100 µl of the IPLC mobile phase (methanol:water:acetic acid, 82:18:0.1 vol/vol/vol). A 20-µl aliquot of the derivatized sample was separated on a 4.6× 250-mm Sym-metry C18 reverse-phase HPLC column (Waters, Milford, Mass.) isocratically, at a rate of 1.3 ml/min using methanol:water:acetic acid at 82:18:0.1 vol/vol/vol as a mobile phase. We tested various other C18 reverse-phase HPLC columns and found that the Symmetry column was the only one that could resolve all of the labeled P-450 metabolites of AA from each other. Fluorescence intensity was continuously monitored using a fluorescence detector (model L-7480; Hitachi, Naperville, Ill.) at a medium gain sensitivity. The amount of 20-HETE in the sample was determined by comparing the area of the 20-HETE peak to that of an internal standard. Between samples, the column was flushed for 10 min with a solution containing methanol plus 50% tetrahydrofuran to remove any residual labeled fatty acids.

4. GC-MS Confirmation of Labeled 20-HETE Peak.

20-HETE (10 ng) was added to a 1-ml sample and derivatized with 2-(2,3-naphthalimino)ethyl trifluoromethanesulfonate. The fraction containing the fluorescent peak (retention time 41 min) was collected and dried under argon. The derivatized sample was redissolved in 49.95% methanol, 49.95% water, and 0.1% formic acid and introduced into an electrospray mass spectroscopy source at a rate of 5 µl/min using a Harvard syringe pump (Harvard Apparatus, South Natick, Mass.). Mass spectral data were acquired over a mass-to-charge ratio range of 200–1,200 at the rate of 5 s/scan with a Quattro II triple quadropole mass spectrometer (Micromass, Manchester, UK) fitted with an electrospray source.

5. Biological Validation of the 20-HETE Assay.

Experiments were performed on 10- to 12-wk-old male Sprague-Dawley rats and spontaneously hypertensive rats (SHR) purchased from Harlan Sprague Dawley (Indianapolis, Ind.). The rats were housed in pairs in a dedicated animal facility with a 12:12-h light-dark cycle and allowed free access to a standard rat chow and drinking water. All procedures were approved by the Animal Care and Use Committee at the Medical College of Wisconsin.

6. Effects of an Irreversible P-450 Inhibitor on the Urinary Excretion of 20-HETE.

SHR and normotensive Sprague-Dawley rats were placed in special metabolic cages (model 650-00350; Nalgene, Rochester, N.Y.) that efficiently separated urine from food and feces and were allowed to equilibrate for 5 days. After 5 days, the food was withdrawn from the rat to prevent contamination of the urine sample and a 24-h control urine sample was collected on dry ice. After the control sample was collected, food was returned to the rats, and after a 2-day recovery period, the rats received an intraperitoneal injection of ABT (50 mg/kg) followed by a second (50 mg/kg) injection 12 h later. Two hours after administration of the first dose of ABT, food was withdrawn and a 24-h experimental urine sample was collected on dry ice. After the urine was collected, the rats were killed with pentobarbital sodium (100 mg/kg ip), and the kidneys were collected. The renal cortex was separated from the renal medulla, frozen in liquid nitrogen, and stored overnight for measurement of the renal metabolism of AA. Briefly, the renal cortex was homogenized in a 10 mM potassium phosphate buffer (pH 7.7) containing 250 mM sucrose, 1 mM EDTA, and 10 mM magnesium chloride, and microsomes were prepared by differential centrifugation. P-4504A enzyme activity was assayed by incubating renal cortical microsomes (0.5 mg) for 15 min at 37° C. with [1-$^{14}$C]AA (0.1 µCi, 42 mM; Amersham, Arlington Heights, Ill.) in 1 ml of a 0.1 M potassium phosphate buffer (pH 7.4) containing 1 mM NADPH as previously described. Ma Y H et al., *Am J Physiol Regulatory Integrative Comp Physiol* 267: R579–R589 (1994). The reactions were terminated by acidification to pH 4 using 0.1 M formic acid and extracted with ethyl acetate. Metabolites were separated using a 25–cm× 2-mm inner diameter (Supelco, Bellefonte, Pa.) C18 reverse-phase HPLC column and a linear elution gradient ranging from acetonitrile:water:acetic acid (50:50:0.1 vol/vol/vol) to acetonitrile:acetic acid (100:0.1 vol/vol) over a 40-min period. The radioactive products were monitored using a radioactive flow detector (model 120; Radiomatic Instrument, Tampa, Fla.).

7. Measurement of 20-HETE Levels in Renal Interstitial Fluid of Anesthetized Rats.

Male Sprague-Dawley rats were anesthetized with ketamine (30 mg/kg im) and Inactin (50 mg/kg ip). The femoral artery and vein were cannulated for measurement of blood pressure and intravenous infusions, and the ureters were cannulated for collection of urine. The animal received an intravenous infusion of 0.9% NaCl containing 1% albumin at a rate of 6 ml/h during the experiment. A microdialysis probe (Bioanalytical Systems, West Lafayette, Ind.) was implanted 3 mm deep into the renal cortex of the left kidney and perfused with sterile saline at a rate of 10 µl/min. The animal was allowed to equilibrate for 1 h, and urine and microdialysis fluid were collected on ice for 1 h.

8. Statistics.

Data presented are means ±SE; n is the number of samples measured. The significance of differences in mean values was analyzed using a paired or unpaired t-test. A $p<0.05$ was considered to be statistically significant.

Results

1. Assessment of the Efficiency of the Extraction Procedure and Labeling Reaction.

Experiments were performed to determine the recovery of $^{14}$C-labeled 20-HETE following extraction from urine with ethyl acetate and partial purification using a Sep-Pak Vac column. Mean recovery of labeled 20-HETE averaged 95±3% (n=6).

The effects of dye concentration and reaction time on the efficiency of the fluorescent derivatization reaction were also evaluated. $^{14}$C-labeled 20-HETE was derivatized with 2-(2, 3-naphthalimino)ethyl trifluoromethanesulfonate, and the fraction of fluorescently labeled and unreacted 20-HETE was determined by HPLC using a fluorescence detector (model L-7480, Hitachi) and a radioactivity detector (model 120; Radiomatic Instrument, Tampa, Fla.) arranged in series. The fluorescent and radioactive peaks coeluted (FIG. 1), indicating that the fluorescent peak was derivatized $^{14}$C-labeled 20-HETE. The absence of a radioactive peak at 10 min, which corresponds to the retention time of unreacted $^{14}$C-labeled 20-HETE, indicates that the fluorescent labeling reaction was complete under the present experimental conditions. In other experiments, we determined that the labeling reaction did not reach completion, and two radiolabeled peaks were seen when the concentration of dye in the reaction was reduced or the reaction time was shortened to 10 min.

2. Separation of Fluorescently Labeled 20-HETE.

Figure 2:
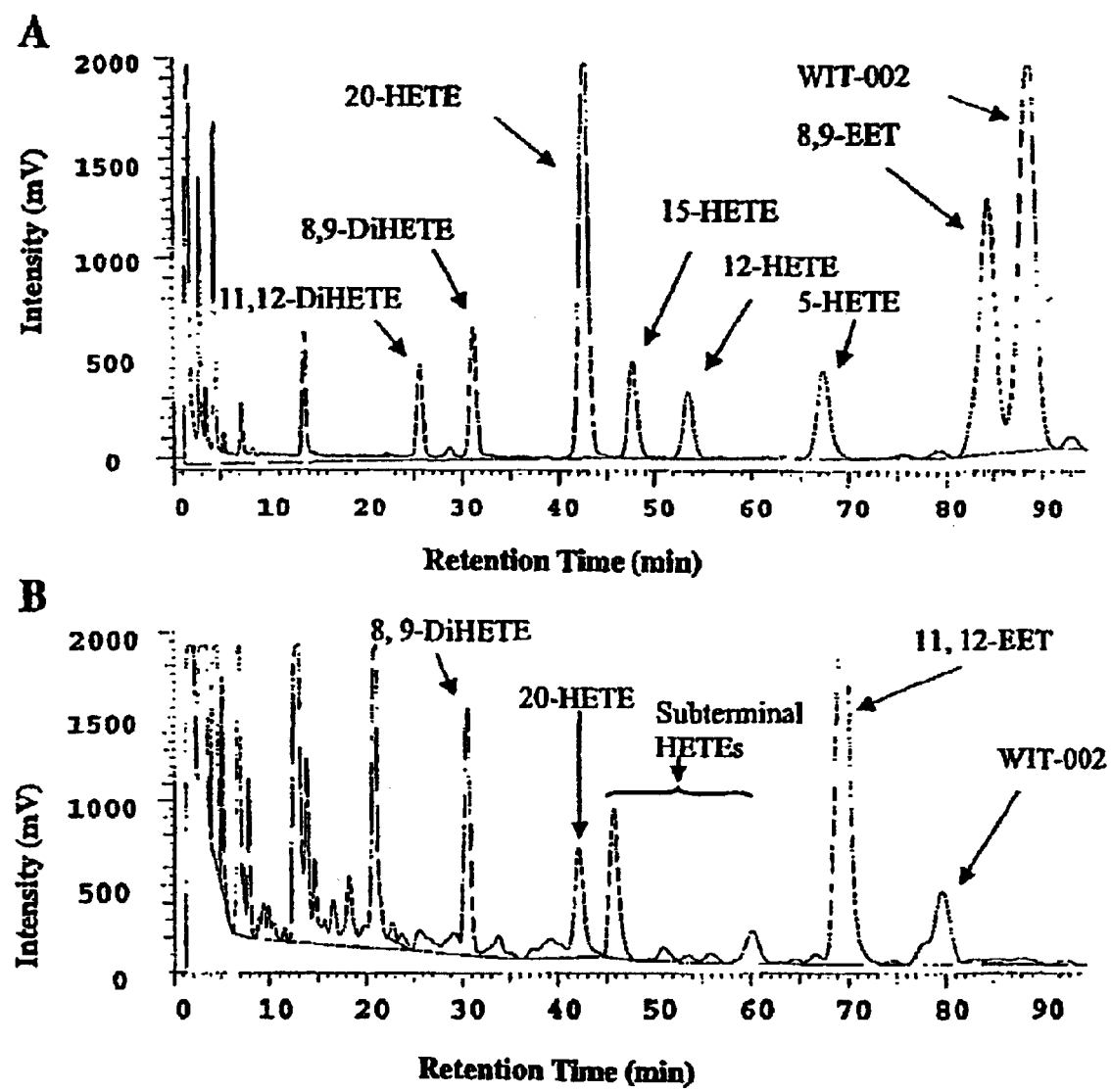
FIG. 2 shows representative HPLC chromatograms illustrating the separation of fluorescently labeled 20-HETE from other P-450 metabolites of arachidonic acid in a mixture of standards (A) and in a labeled sample (0.3 ml) of rat urine (B).

A typical HPLC chromatogram illustrating the separation of the 20-HETE peak from other structurally similar P-450 metabolites of AA is presented in FIG. 2A. Abbreviations used in FIG. 2 include: EET, epoxyeicosatrienoic acid; diHETE, hydroxyeicosatetraenoic acid; WIT-002, 20-hydroxyeicosa-6(Z),15(Z)-dienoic acid. As shown in FIG. 2A, fluorescently labeled 20-HETE elutes with a retention time of 41 min and is clearly separated from the peaks corresponding to labeled 14,15- and 8,9-diHETE, 15-, 12-, and 5-HETE, and 8,9-EET. A more complete listing of the retention times of all the other biologically relevant P-450 metabolites of AA and other potential interfering endogenous fatty acids that we tested is presented in Table 1. Even some of the compounds that are quite difficult to resolve from unlabeled 20-HETE, such as 19-, 18-, and 16-HETE and 5,6- and 8,9-di-HETE, can be easily resolved from fluorescently labeled 20-HETE using this HPLC system. The following abbreviations are used in Table 1: DiHETE, dihydroxyeicosatetraenoic acid; ETYA, 5,8,11,14-eicosatetraynoic acid; HETE, hydroxyeicosatetraenoic acid; EET, epoxyeicosatrienoic acid; WIT-002, 20-hydroxyeicosa-6(Z),15(Z)-dienoic acid; and C19 analog, 19-hydroxynonadeca-5(Z),8(Z),11(Z),14(Z)-tetranoic acid.

A typical chromatogram of a derivatized sample of urine collected from a conscious rat is presented in FIG. 2B. This sample contains peaks for 11,12-EET and 8,9-diHETE and 20-HETE. It also contains peaks corresponding to the retention times of the subterminal HETEs (18-, 17-, 16-, 15-, 12-, and 5-HETE), and EETs. The peak seen at 80 min corresponds to the retention time of the internal standard, WIT-002. There is a small peak that appeared at 70 min when blank samples containing only dye and catalyst were injected. It therefore represents either a contaminant in the reagents or a fluorescent product formed from the dye and the catalyst. Unfortunately, this contaminant coelutes with 11,12-EET, an important P-450 metabolite of AA. However, the magnitude of this blank peak is usually small (<150 mV) and can be subtracted from sample chromatograms by the computer.

Figure 3:
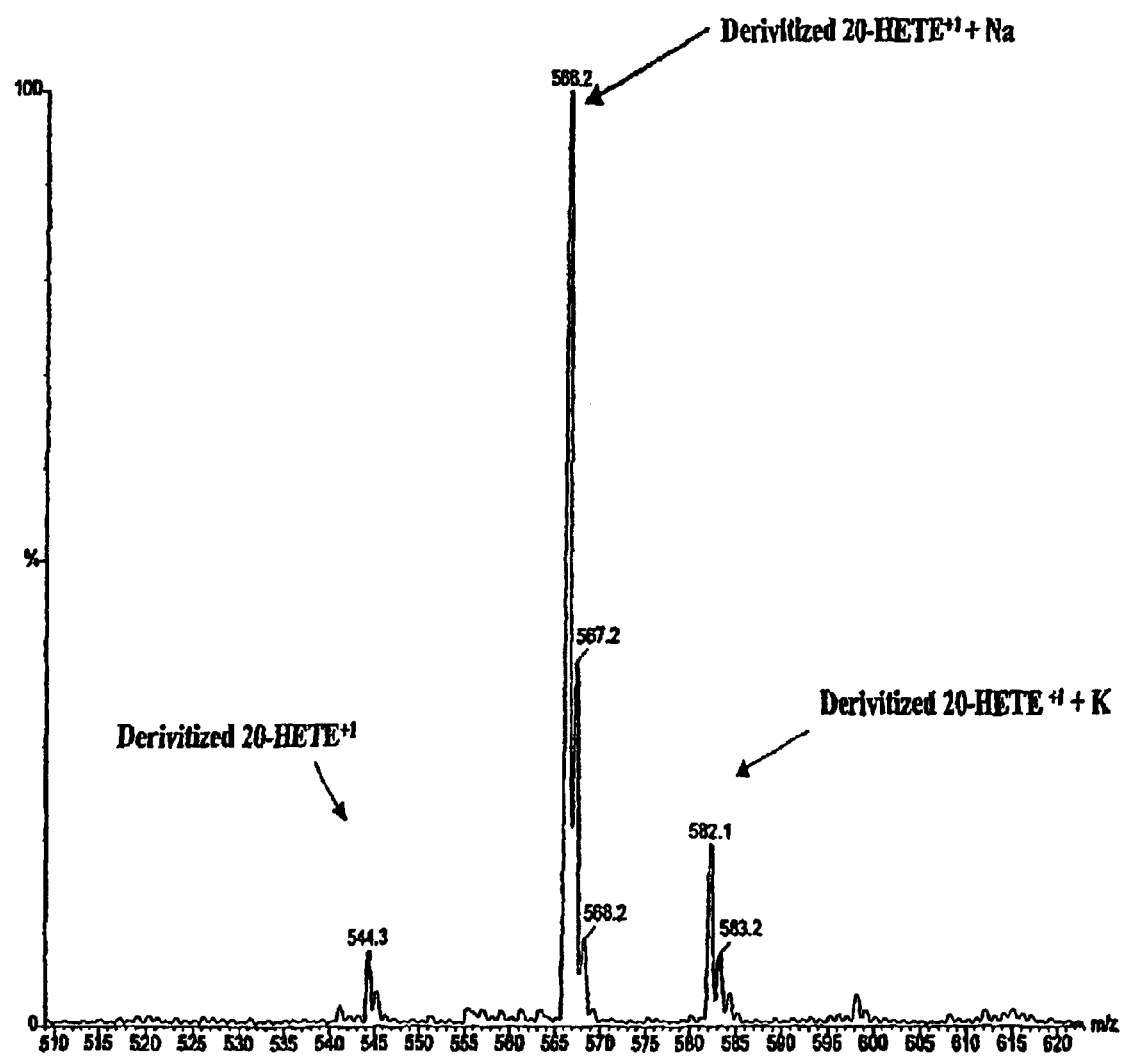
FIG. 3 is a liquid chromatography-gas chromatography chromatogram of the 41-min HPLC peak corresponding to the retention time of fluorescently labeled 20-HETE.

Other experiments were performed to confirm that the peak that elutes at 41 min was labeled 20-HETE. In these experiments, 20-HETE (100 ng/ml) was added to a blank sample, extracted, and derivatized, and the 41-min peak was collected and analyzed using liquid chromatography (LC)-GC-MS. The results of these experiments, presented in FIG. 3, confirm that this peak consists of a compound with mass-to-charge ratios (m/z) of 544, 566, and 584, corresponding to the expected mass-to-charge ratios of fluorescently labeled 20-HETE, 20-HETE plus a sodium ion, and 20-HETE plus a potassium ion, respectively.

TABLE 1

Retention times of major P-450 metabolites of arachidonic acid and 20-HETE analogs.

| P-450 Metabolites Retention | Times, min |
|---|---|
| 14,15-diHETE | 22 |
| 11,12-diHETE | 25 |
| C19 analog | 28 |
| 15-Hydroxypentadecanoic acid | 30 |
| 8,9-diHETE | 30 |
| ETYA | 35 |
| 5,6-diHETE | 35 |
| 19-HETE | 39 |
| 20-HETE | 41 |
| 16-Hydroxyhexadecanoic acid | 42 |
| 18-HETE | 43 |
| 17-HETE | 45 |
| 16-HETE | 45 |
| 15-HETE | 46 |

TABLE 1-continued

Retention times of major P-450 metabolites of arachidonic acid and 20-HETE analogs.

| P-450 Metabolites Retention | Times, min |
|---|---|
| 10-Hydroxyhexadecanoic acid | 47 |
| 12-HETE | 49 |
| 5-HETE | 62 |
| Dimethyl 20-HETE | 65 |
| 14,15-EET | 68 |
| 11,12-EET | 70 |
| 8,9-EET | 78 |
| PS C19 analog | 79 |
| WIT-002 | 81 |
| 5,6-EET | 90 |

3. 20-HETE Assay.

Figure 4:
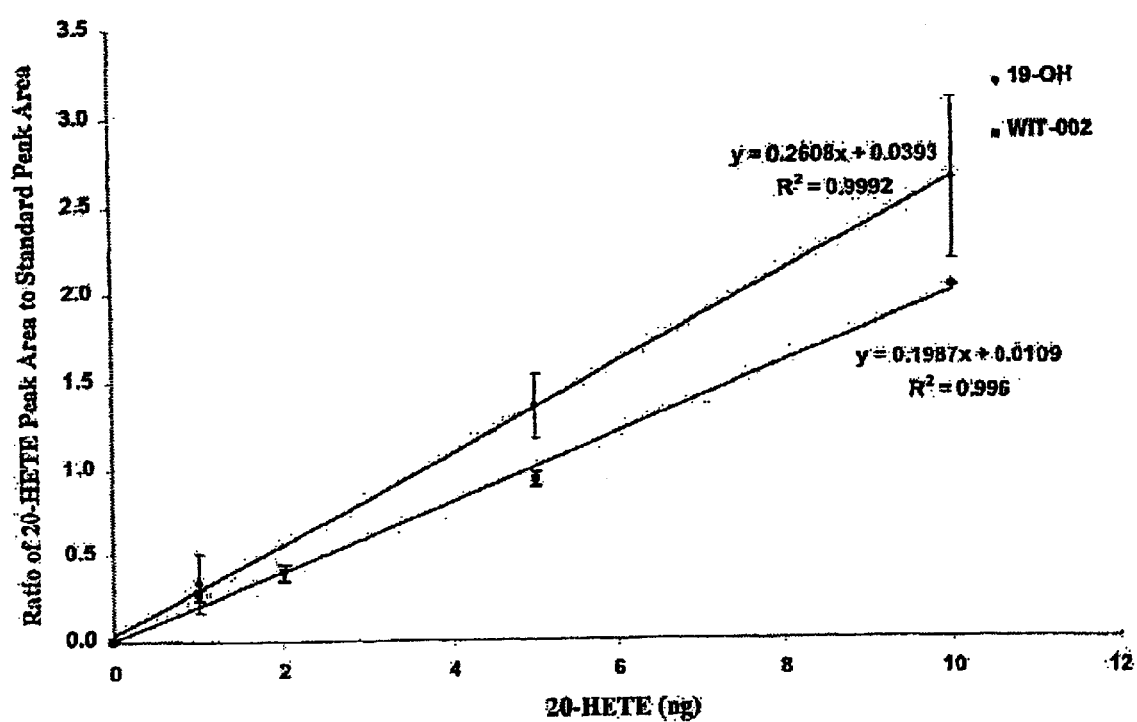
FIG. 4 shows standard curves relating the ratio of areas of peaks to 20-HETE and internal standards, either 19-hydroxynonadeca-5(Z),8(Z), 11(Z), 14(Z)-tetraenoic acid (19-OH) or WIT-002.

Standard curves were generated, in which samples containing various amounts of 20-HETE (5–200 ng/ml) and 100 ng/ml of an internal standard, either WIT-002 or 19-hydroxynonadeca-5(Z),8(Z),11(Z),14(Z)-tetraenoic acid, were extracted and fluorescently labeled with 2-(2,3-naphthalimino)ethyl trifluoromethanesulfonate. Aliquots of these samples containing 1–10 ng of 20-HETE and 5 ng of the internal standard were separated by reverse-phase HPLC using an isocratic elution with 82% methanol:water at a rate of 1.3 ml/h. The ratio of the areas of the 20-HETE and internal standard peaks were plotted against the amount of 20-HETE in the aliquot and are presented in FIG. 4. The ratio of peak areas was highly correlated to the expected amount of 20-HETE in the sample ($r^2$=0.98). Correlation coefficients averaged 0.99 for the curve relating 20-HETE and 19-OH (n=3 samples) and 0.99 for the curve relating 20-HETE and WIT-002 (n=3 samples). The slopes of the curves were 0.19 for WIT-002 and 0.26 for 19-hydroxynonadeca-5(Z),8(Z),11(Z),14(Z)-tetraenoic acid. These coefficients are within errors associated with the addition of equal nanogram amounts of standards to samples and, for all practical purposes, indicate that 20-HETE and these two closely related analogs label with equal efficiency. This is not the case with all compounds. For example, we found that other fatty acids that do not have a double bond near the carboxyl group, such as linolenic and y-linolenic acids, and other unsaturated fatty alcohols, such as 10-hydroxyhexadecanoic acid, 16-hydroxyhexadecanoic acid, or 15-hydroxypentadecanoic acid, label with a much higher efficiency (typically 3:1) than 20-HETE, HETEs, and EETs. They are also not extracted from biological samples with the same efficiency as 20-HETE.

Figure 5:
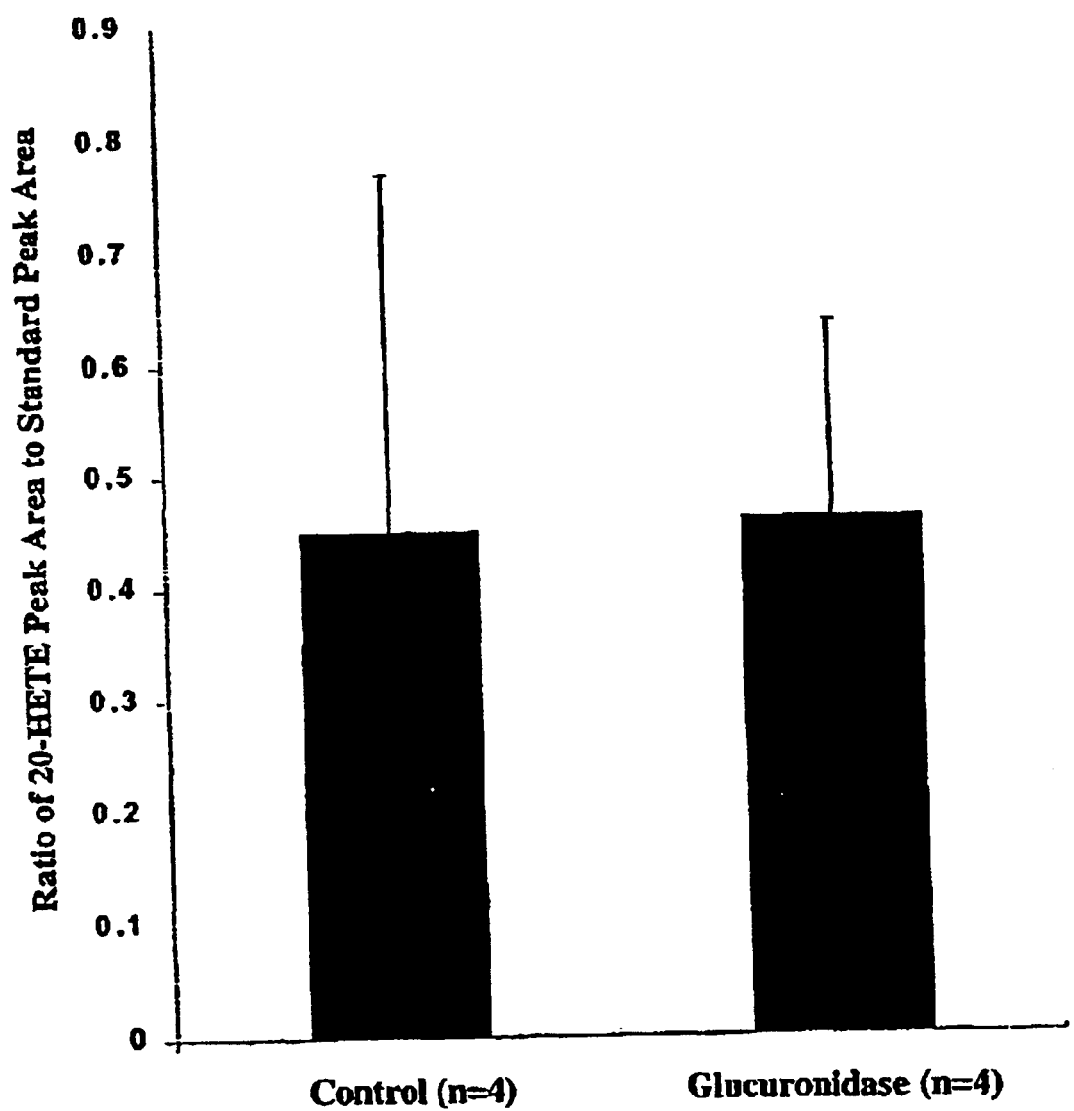
FIG. 5 shows effects of treatment of rat urine samples with glucuronidase on the concentration of 20-HETE.

Previous studies have indicated that the majority of 20-HETE and other RETEs in human urine is excreted as a glucuronide. Prakash C et al., Biochem Biophys Res Commun 185: 728–733 (1992). We therefore examined the effects of treatment of rat urine samples with glucuronidase (50 units/ml) at 37° C. for 1 h on the concentration of 20-HETE. The results are presented in FIG. 5. Values are means ±SE; n=no. of samples measured. There was no significant difference in the 20-HETE level measured before and after treatment of the samples with glucuronidase.

We also measured 20-HETE levels after adding known amounts of this compound to urine samples and determined the intra-assay variation of the assay. Mean recovery of 20-HETE added to samples of rat urine was 95±3% (n=6). Intra-assay variation in repeated measurements of the same sample of urine made over a period of several days averaged 4.7±1% (n=6).

4. Effect of a P-450 Inhibitor on the Urinary Excretion of 20-HETE.

Figure 6:
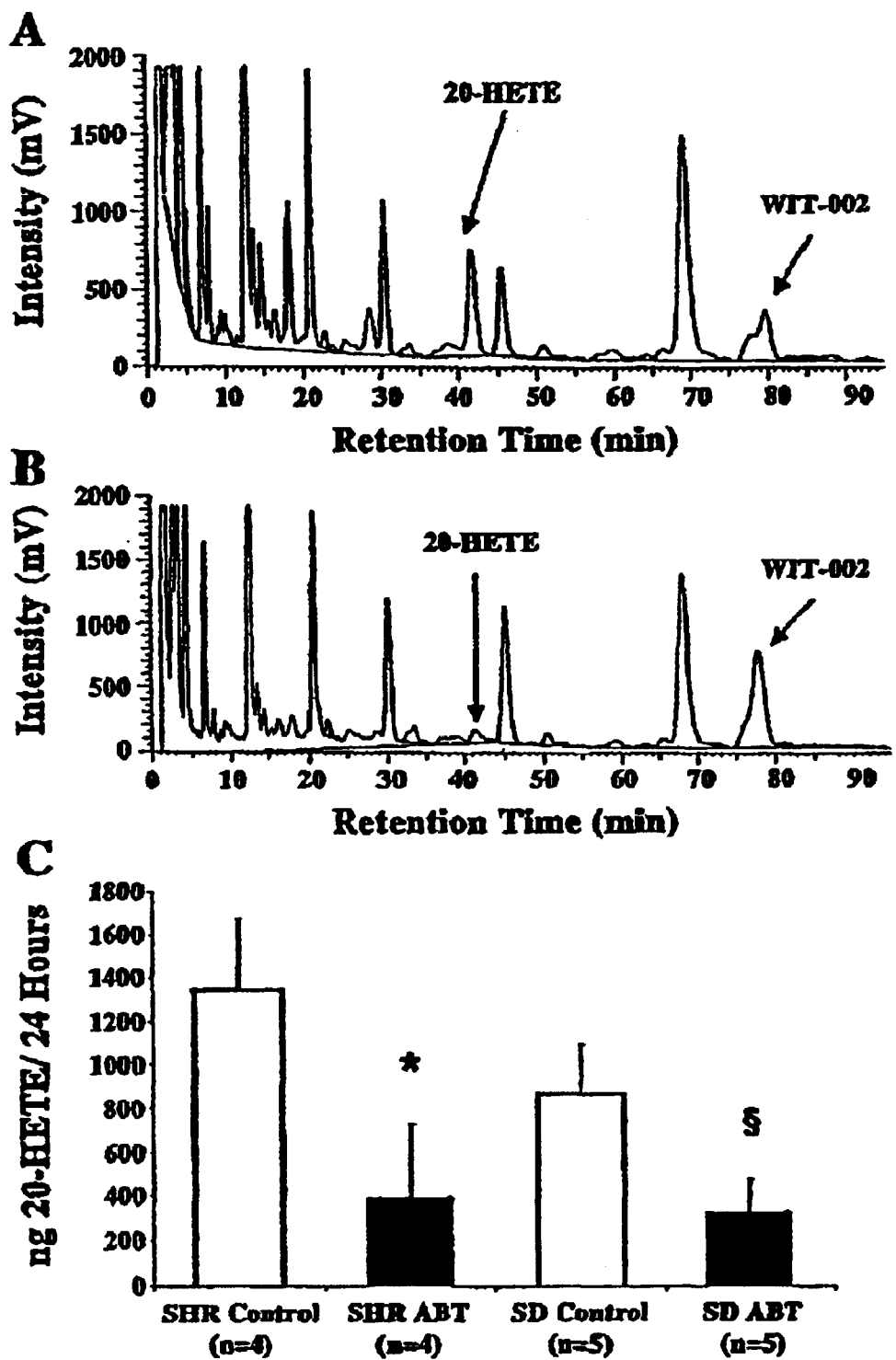
FIG. 6 shows effects of blockade of the renal formation of 20-HETE with 1-aminobenzotriazole (ABT; 50 mg/kg) on the urinary excretion of 20-HETE in spontaneously hypertensive rats (SHR) and Sprague-Dawley rats (SD).

The effect of ABT on urinary excretion of 20-HETE in SHR and Sprague-Dawley rats is presented in FIG. 6. Values are means ±SE; n=no. of samples measured; *,§ indicate significant difference from control within a group. Control urinary excretion of 20-HETE was significantly higher in SHR (n=4) than in Sprague-Dawley rats (n=5) and averaged 1,334±337 and 872±338 ng/day, respectively. The excretion of 20-HETE fell by 65±10% after administration of ABT to SHR and by 74±9% in Sprague-Dawley rats. The change in the urinary excretion of 20-HETE paralleled the fall in the renal production of 20-HETE in microsomes prepared from the kidneys of these animals. In this regard, 20-HETE production by renal cortical microsomes averaged 459±192 and 12±4 pmol•min$^{-1}$•mg$^{-1}$ in vehicle- and ABT-treated SHR (n=4), respectively. Similarly, 20-HETE production fell from 324±25 to 25±3 pmol•min$^{-1}$•mg$^{-1}$ in microsomes prepared from the kidneys of vehicle- and ABT-treated Sprague-Dawley rats (n=5).

5. Measurement of 20-HETE Levels in Renal Interstitial Fluid and Renal Cortical Tissue.

Experiments were also performed to determine whether the assay was sensitive enough to measure the levels of 20-HETE and other P-450 metabolites of AA in 100 μl of fluid collected from a microdialysis capsule acutely implanted in the renal cortex and brain of rats and perfused with sterile saline at 5 μl/min. 20-HETE, diHETEs, and EETs could be detected in samples collected from both the kidney and the brain. In the kidney, basal 20-HETE concentration averaged 3.1 ±0.3 ng/ml (n=4). This finding compared with a concentration of 20-HETE in renal cortical tissue of 1.8±0.3 ng/g of tissue (n=3). In microdialysis fluid collected from the brain of rats, we found that the concentrations of 20-HETE and diHETEs averaged 27±3 and 39±1 ng/ml, respectively (n=5).

We claim:

1. A method for analyzing P-450 metabolites of arachidonic acid from a biological sample, comprising the steps of:
   extracting P-450 metabolites of arachidonic acid from the sample;
   labeling P-450 metabolites of arachidonic acid with a fluorescent material;
   loading P-450 metabolites of arachidonic acid labeled with the fluorescent material onto a 4.5×250-mm, 5 μM particle size C18 reverse-phase HPLC column;
   passing a mobile phase of methanol:water:acetic acid with a volume ratio of about 82:18:0.1 through the column isocratically at a rate of about 1.3 ml per minute; and
   monitoring fluorescence intensity of eluent.

2. The method of claim 1, further comprising the step of:
   purifying P-450 metabolites of arachidonic acid after extracting them from the sample but before labeling them.

3. The method of claim 1, further comprising the step of:
   purifying P-450 metabolites of arachidonic acid labeled with the fluorescent material after labeling P-450 metabolites of arachidonic acid with the fluorescent material but before loading them onto the HPLC column.

4. The method of claim 1, wherein the fluorescent material is 2-(2,3-naphthalimino)ethyl trifluoromethanesulfonate.

5. The method of claim 1, wherein the labeling is catalyzed by a catalyst.

6. The method of claim 5, wherein the catalyst is selected from the group consisting of a combination of potassium fluoride and 18-crown-6, a combination of potassium fluoride and tetraethylammonium carbonate, and N,N-diisopropylethylamine.

7. The method of claim 5, wherein the catalyst is N,N-diisopropylethylamine.

8. The method of claim 1, wherein the biological sample is selected from the group consisting of urine, blood, plasma, cerebrospinal fluid, bronchiolar lavage fluid and a tissue.

9. The method of claim 8, wherein the tissue is selected from the group consisting of renal tissue, brain tissue, lung tissue, liver tissue, breast tissue and biopsies from suspected cancerous tumors.

10. A method for analyzing P-450 metabolites of arachidonic acid in a biological sample, comprising the steps of:
    adding an internal standard into the sample;
    extracting P-450 metabolites of arachidonic acid and the added internal standard from the sample;
    labeling P-450 metabolites of arachidonic acid and the internal standard with a fluorescent material;
    loading P-450 metabolites of arachidonic acid and the internal standard, both of which are labeled with the fluorescent material, onto a 4.5×250-mm, 5 μM particle size C18 reverse-phase HPLC column;
    passing a mobile phase of methanol:water:acetic acid with a volume ratio of about 82:18:0.1 through the column isocratically at a rate of about 1.3 ml per minute;
    monitoring fluorescence intensity of eluent; and
    quantitating P-450 metabolites of arachidonic acid by calculating the peak ratio of a metabolite to the internal standard.

11. The method of claim 10, wherein the internal standard is a nonbiologically relevant hydroxy fatty acid.

12. The method of claim 11, wherein the nonbiologically relevant hydroxy fatty acid is selected from the group consisting of WIT-002, 19-hydroxynonadeca-5(Z),8(Z),11(Z),14(Z)-tetraenoic acid, 10-hydroxyhexadecanoic acid tridecanoic acid, 16-hydroxyhexadecanoic acid tridecanoic acid, 15-hydroxypentadecanoic acid and tridecanoic acid.

13. The method of claim 10, wherein the internal standard is selected from the group consisting of WIT-002 and 19-hydroxynonadeca-5(Z),8(Z), 11(Z), 14(Z)-tetraenoic acid.

14. The method of claim 10, wherein the quatitating step is aided by a computer.

15. The method of claim 10, wherein the fluorescence material is 2-(2,3-naphthalimino)ethyl trifluoromethanesulfonate.

16. The method of claim 10, wherein the labeling is catalyzed by a catalyst.

17. The method of claim 16, wherein the catalyst is selected from the group consisting of a combination of potassium fluoride and 18-crown-6, a combination of potassium fluoride and tetraethylammonium carbonate, and N,N-diisopropylethylamine.

18. The method of claim 16, wherein the catalyst is N,N-diisopropylethylamine.

19. The method of claim 10, wherein the biological sample is selected from the group consisting of urine, blood, plasma, cerebrospinal fluid, bronchiolar lavage fluid and a tissue.

20. The method of claim 19, wherein the tissue is selected from the group consisting of renal tissue, brain tissue, lung tissue, liver tissue, breast tissue and biopsies from suspected cancerous tumors.

21. A method for clinically diagnosing of a disease associated with abnormalities in arachidonic acid metabolism, comprising the step of:

analyzing P-450 metabolites of arachidonic acid from a sample of a human being comprising the steps of:
extracting P-450 metabolites of arachidonic acid from the sample;
labeling P-450 metabolites of arachidonic acid with a fluorescent material;
loading P-450 metabolites of arachidonic acid labeled with the fluorescent material onto a 4.5×250-mm, 5 μM particle size C18 reverse-phase HPLC column;
passing a mobile phase of methanol:water:acetic acid with a volume ratio of about 82:18:0.1 through the column isocratically at a rate of about 1.3 ml per minute; and
monitoring fluorescence intensity of eluent.

22. The method of claim 21, wherein the disease associated with abnormalities in arachidonic acid metabolism is selected from the group consisting of salt sensitive hypertension, toxemia of pregnancy, asthma, hepatorenal syndrome, diabetes and subarachnoid hemorrhage.

23. A method for clinically diagnosing of a disease associated with abnormalities in arachidonic acid metabolism, comprising the step of:

analyzing P-450 metabolites of arachidonic acid from a sample of a human being comprising the steps of:
adding an internal standard into the sample;
extracting P-450 metabolites of arachidonic acid and the added internal standard from the sample;
labeling P-450 metabolites of arachidonic acid and the internal standard with a fluorescent material;
loading P-450 metabolites of arachidonic acid and the internal standard, both of which are labeled with the fluorescent material, onto a 4.5×250-mm, 5 μM particle size C18 reverse-phase HPLC column;
passing a mobile phase of methanol:water:acetic acid with a volume ratio of about 82:18:0.1 through the column isocratically at a rate of about 1.3 ml per minute;
monitoring fluorescence intensity of eluent; and
quantitating P-450 metabolites of arachidonic acid by calculating the peak ratio of a metabolite to the internal standard.

24. The method of claim 23, wherein the disease associated with abnormalities in arachidonic acid metabolism is selected from the group consisting of salt sensitive hypertension, toxemia of pregnancy, asthma, hepatorenal syndrome, diabetes and subarachnoid hemorrhage.

25. A method for labeling P-450 metabolites of arachidonic acid, comprising the step of:

mixing P-450 metabolites of arachidonic acid, 2-(2,3-naphthalimino)ethyl trifluoromethanesulfonate and N,N-diisopropylethylamine.

* * * * *

UNITED STATES PATENT AND TRADEMARK OFFICE
CERTIFICATE OF CORRECTION

PATENT NO. : 6,764,855 B2
DATED : July 20, 2004
INVENTOR(S) : Richard J. Roman et al.

It is certified that error appears in the above-identified patent and that said Letters Patent is hereby corrected as shown below:

Column 5,
Lines 19 and 20, "BETE" should be -- HETE --.
Line 56, "IPLC" should be -- HPLC --.

Column 6,
Line 52, "tetraethylanunonium" should be -- tetraethylammonium --.

Column 7,
Line 4, "IPLC" should be -- HPLC --.

Column 10,
Line 52, "RETES" should be -- HETES --.

Signed and Sealed this

Twenty-first Day of December, 2004

JON W. DUDAS
*Director of the United States Patent and Trademark Office*